US00PP16908P2

(12) United States Plant Patent
Herdegen

(10) Patent No.: US PP16,908 P2
(45) Date of Patent: Aug. 1, 2006

(54) ***EUPHORBIA* PLANT NAMED 'IMPREFANT'**

(50) Latin Name: *Euphorbia hybrida*
Varietal Denomination: Imprefant

(75) Inventor: Susanne Herdegen, Dexheim (DE)

(73) Assignee: InnovaPlant GmbH & Co. KG, Gensingen (DE)

( * ) Notice: Subject to any disclaimer, the term of this patent is extended or adjusted under 35 U.S.C. 154(b) by 0 days.

(21) Appl. No.: 11/113,385

(22) Filed: Apr. 23, 2005

(51) Int. Cl.
*A01H 5/00* (2006.01)

(52) U.S. Cl. ..... Plt./302

(58) Field of Classification Search ..... Plt./302, Plt./226

See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Euphorbia* plant named 'Imprefant', characterized by its compact and mounded plant habit; freely branching habit; burgundy-colored young foliage; resistance to Powdery Mildew; and good garden performance.

1 Drawing Sheet

Botanical designation: *Euphorbia hybrida.*
Cultivar denomination: 'Imprefant'.

BACKGROUND OF THE INVENTION

The present Invention relates to a new and distinct cultivar of *Euphorbia* plant, botanically known as *Euphorbia hybrida*, and hereinafter referred to by the cultivar named Imprefant.

The new *Euphorbia* is a product of a planned breeding program conducted by the Inventor in Gensingen, Germany. The objective of the breeding program is to create new compact *Euphorbia* plants with attractive foliage coloration and tolerance to Powdery Mildew.

The new *Euphorbia* originated from a cross-pollination made by the Inventor in May, 1999 of an unnamed selection of *Euphorbia×martinii*, not patented, as the female, or seed parent, with the *Euphorbia amygdaloides* cultivar Purpurea, not patented, as the male, or pollen parent. The new *Euphorbia* was discovered and selected as a single plant from within the resulting progeny of the cross-pollination in Gensingen, Germany in September, 1999.

Asexual reproduction of the new cultivar by terminal vegetative cuttings since May, 2000 in Gensingen, Germany has shown that the unique features of this new *Euphorbia* are stable and reproduced true to type in successive generations.

SUMMARY OF THE INVENTION

Plants of the cultivar Imprefant have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Imprefant'. These characteristics in combination distinguish 'Imprefant' as a new and distinct cultivar:

1. Compact and mounded plant habit.
2. Freely branching habit.

3. Burgundy-colored young foliage.
4. Resistant to Powdery Mildew.
5. Good garden performance.

In side-by-side comparisons conducted in Gensingen, Germany, plants of the new *Euphorbia* differ primarily from plants of the parents in plant growth habit as plants of the new *Euphorbia* are more compact and not as vigorous as plants of the parents. In addition, under low temperatures, leaves of plants of the male parent, the cultivar Purpurea, become twisted, whereas leaves of plants of the new *Euphorbia* do not become twisted under low temperatures.

Plants of the new *Euphorbia* can be compared to plants of the *Euphorbia* cultivar Efanthia, not patented. In side-by-side comparisons conducted in Gensingen, Germany, plants of the new *Euphorbia* differed from plants of the cultivar Efanthia in the following characteristics:

1. Plants of the new *Euphorbia* were more compact than plants of the cultivar Efanthia.
2. Plants of the new *Euphorbia* were more resistant to Powdery Mildew than plants of the cultivar Efanthia.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanial description which accurately describe the colors of the new *Euphorbia.*

The photograph at the top of the sheet is a close-up view of typical leaves of 'Imprefant'.

The photograph at that bottom of the sheet comprises a side perspective view of a typical plant of 'Imprefant' grown in a container.

DETAILED BOTANICAL DESCRIPTION

The aforementioned photographs and following observations and measurements describe plants grown in Bonsall, Calif., in an outdoor nursery during the fall and winter under full sun conditions with day temperatures ranging from 13 to 35° C. and night temperatures ranging from 4 to 19° C. After planting rooted cuttings, plants were grown for about 19 weeks in 12.5-cm containers. Plants were pinched one time. Color references are made to The Royal Horticultural Society Colour Chart, 1995 Edition, except where general terms of ordinary dictionary significance are used.

Botanical classification: *Euphorbia hybrida* cultivar Imprefant.

Parentage:

*Female*.—Unnamed selection of *Euphorbia×martinii*, not patented.

*Male parent*.—*Euphorbia amygdaloides* cultivar Purpurea, not patented.

Propagation:

*Type*.—By cuttings.

*Time to initiate roots, summer*.—About 14 days at temperatures of 20° C.

*Time to initiate roots, winter*.—About 18 days at temperatures of 20° C.

*Time to develop roots*.—About 20 days at temperatures of 20° C.

*Root description*.—Fine, white in color.

*Rooting habit*.—Freely branching.

Plant description:

*Plant form and growth habit*.—Compact and mounded plant habit; upright to somewhat outwardly spreading; inverted triangle; perennial subshrub. Moderate growth rate.

*Branching habit*.—Freely branching, usually about 12 lateral branches develop per plant; dense and bushy plant form.

*Plant height*.—About 22 cm.

*Plant diameter*.—About 34 cm.

*Lateral branch description*.—Length: About 20 cm. Diameter: About 8 mm. Internode length: About 8 mm. Strength: Strong. Texture: Sparsely pubescent. Color: 183A.

Foliage description:

*Arrangement*.—Alternate to whorled; simple.

*Length*.—About 4.2 cm.

*Width*.—About 1.2 cm.

*Shape*.—Obovate to elliptical.

*Apex*.—Rounded.

*Base*.—Attentuate.

*Margin*.—Entire.

*Texture, upper surface*.—Glabrous; smooth.

*Texture, lower surface*.—Pubescence along the midvein.

*Venation*.—Pinnate, arcuate.

*Color*.—Developing foliage, upper surface: 146B. Developing foliage, lower surface: 183B. Fully developed foliage, upper and lower surfaces 147A to 147B tinged with 183A. Venation, upper and lower surfaces: 146C.

*Petiole*.—Length: About 1.2 cm. Diameter: About 1 mm. Texture, upper and lower surfaces: Smooth, glabrous. Color, upper surface: 183D. Color, lower surface: 183A.

Flower description: Flower development has not been observed on plants of the new *Euphorbia*.

Disease/pest resistance: Plants of the new *Euphorbia* have been observed to be resistant to Powdery Mildew. Plants of the new *Euphorbia* not been observed to be resistant to pests and other pathogens common to *Euphorbia*.

Temperature tolerance: Plants of the new *Euphorbia* are tolerant to temperatures as low as −6° C. and as high as 40° C.

It is claimed:

1. A new and distinct *Euphorbia* plant named 'Imprefant', as illustrated and described.

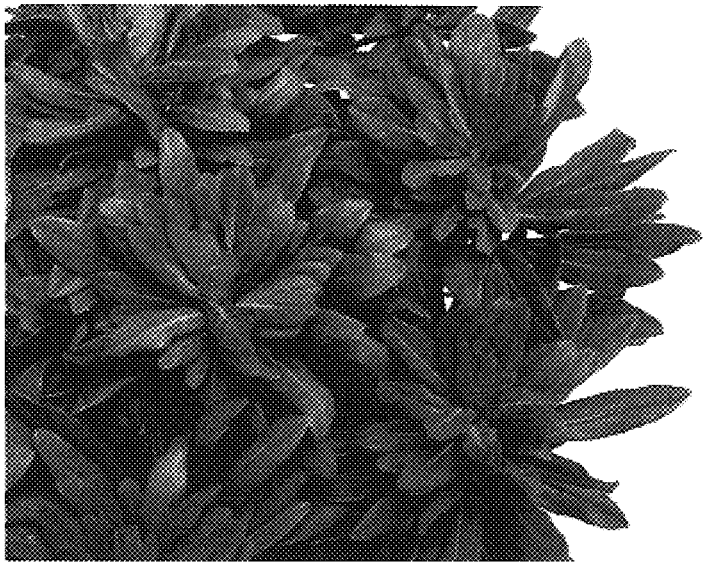
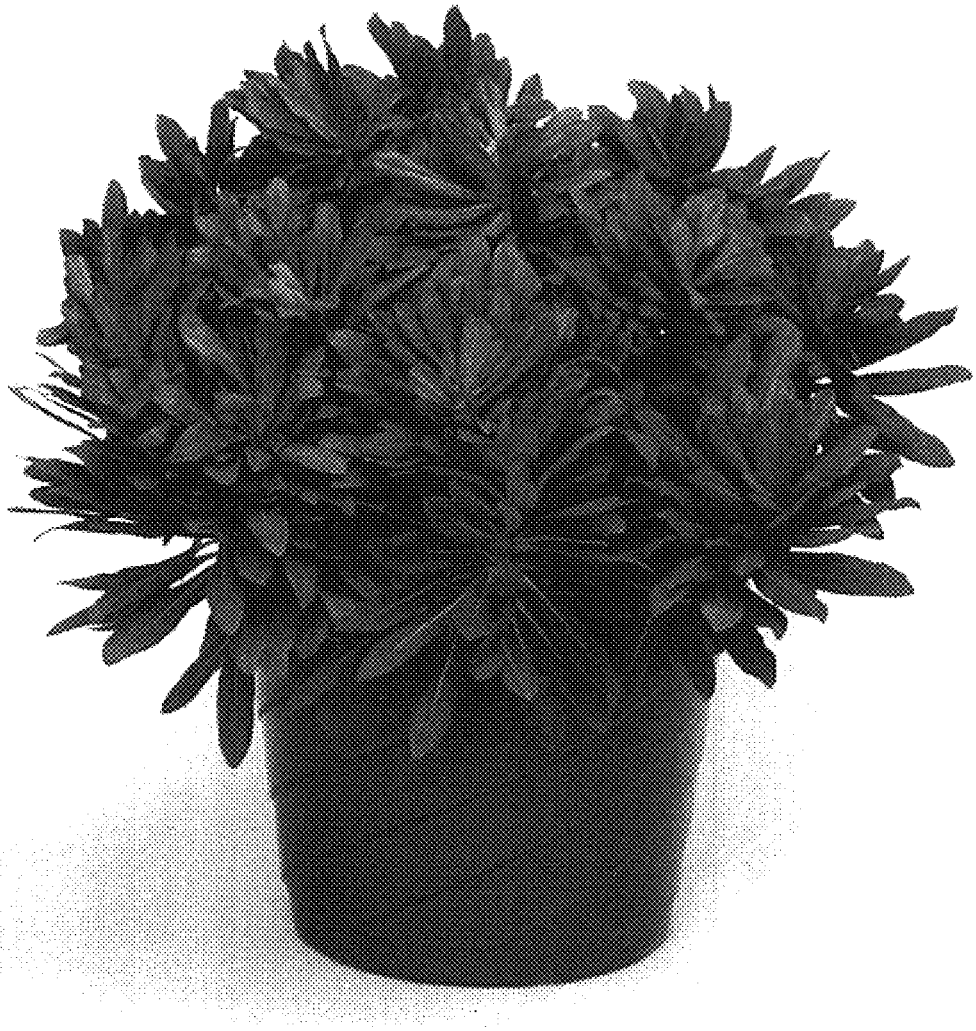

* * * * *